United States Patent [19]

Britten et al.

[11] Patent Number: 4,591,567

[45] Date of Patent: May 27, 1986

[54] RECOMBINANT DNA SCREENING SYSTEM INCLUDING FIXED ARRAY REPLICATOR AND SUPPORT

[75] Inventors: Roy J. Britten, Costa Mesa; Eric H. Davidson, Pasadena, both of Calif.

[73] Assignee: California Institute of Technology, Pasadena, Calif.

[21] Appl. No.: 520,756

[22] Filed: Aug. 8, 1983

Related U.S. Application Data

[63] Continuation-in-part of Ser. No. 370,412, Apr. 21, 1982, abandoned.

[51] Int. Cl.[4] .................. C12M 1/32; C12M 1/26; C12Q 1/68; C12Q 1/24
[52] U.S. Cl. ............................. 435/293; 935/80; 935/86; 435/5; 435/6; 435/30; 435/292; 435/800; 435/809
[58] Field of Search .................. 435/5, 6, 30, 35, 172, 435/292, 293, 294, 800, 809; 935/80, 85, 86

[56] References Cited

U.S. PATENT DOCUMENTS

| | | | |
|---|---|---|---|
| 2,956,931 | 10/1960 | Goldberg | 435/5 |
| 3,787,290 | 1/1974 | Kaye | 435/40 |
| 3,912,596 | 10/1975 | Haque et al. | 435/294 |
| 4,235,971 | 11/1980 | Howard et al. | 435/293 |
| 4,252,897 | 2/1981 | Axford et al. | 435/33 |
| 4,368,272 | 1/1983 | Kashket | 435/30 |
| 4,397,955 | 8/1983 | Entis et al. | 435/30 |

OTHER PUBLICATIONS

Maniatis et al., "Molecular Cloning, a Laboratory Manual", Cold Spring Harbor Laboratory, pp. 304–307, (1982).
Grunstein et al., "Colony Hybridization: A Method for the Isolation of Cloned DNAs that Contain a Specific Gene", Proceedings of the National Academy of Sciences, 72(10), pp. 3961–3965, (1975).
Benton et al., "Screening γgt Recombinant Clones by Hybridization to Single Plaques In Situ", Science, 196, pp. 180–182 (1977).
Chakrabarty, "Genetic Engineering", CRC Press Inc., West Palm Beach, FL, pp. 19–20 (1979).
Kaneko et al., "Multiple Syringe Innoculator for Agar Plates", Applied and Environmental Microbiology, 33(1), pp. 982–985 (1977).

Primary Examiner—Alvin E. Tanenholtz
Assistant Examiner—John E. Tarcza
Attorney, Agent, or Firm—Joseph E. Mueth

[57] ABSTRACT

A system for the production and maintenance of genomic libraries of recombinant DNA in a fixed geometric array arranged so that such libraries may be accurately replicated and maintained with the same set of individual DNA inserts occupying reproducible locations and comprising, (a) sets of individual bacterial colonies or plaques of bacteriophage which contain inserts of animal or plant DNA and are present in so large a number that there will be a high probability that the complete library will contain each DNA sequence of all of the sequences present in an animal or plant genome; to be established in subarrays which can individually be replicated, (b) a subsystem for picking up inocula from each of a geometric array simultaneously and transferring them to a second similar geometric array, including carrying and aligning means for maintaining a transfer means in superposed relationship with respect and for raising and lowering the transfer means into and out of proximity to said colonies or plaques, and (c) a subsystem for intially establishing such subarrays by transfer from a randomly spread pattern of colonies or plaques of bacteriophage.

6 Claims, 8 Drawing Figures

RECOMBINANT DNA SCREENING SYSTEM INCLUDING FIXED ARRAY REPLICATOR AND SUPPORT

This application is a continuation-in-part of application Ser. No. 370,412, filed Apr. 21, 1982, now abandoned.

BACKGROUND OF THE INVENTION

Many of the most fundamental recombinant DNA operations involve gene isolation from recombinant DNA libraries, using radioactively labelled probes. The current procedures derive originally from the autoradiographic plaque screening methods of Benton, W. D. and Davis, R. W. (1977) Science 196, 180–182, as applied to recombinant DNA genome libraries (e.q., Maniatis, T., Hardison, R. C., Lacy, E., Lauer, J., O'-Connel, C., Quon, D., Sim, G. K and Efstratiadis, A. (1978) Cell 15, 687–701. As conventionally carried out sufficient plaques bearing individual recombinant phage are screened so that any given sequence will probably occur several times. For the human genome (3,000,000 kb genome size) an average of three occurrences requires about 500,000 different phage, while for sea urchin or Drosophila genomes the number is smaller (about 130,000 and 50,000, respectively) because of the smaller genome size. In present practice a library is propagated by growth in bacterial lawns on agar plates (often 155 mm in diameter). For each amplification or screening step the plaques are diluted and replated at about 1 phage per mm$^2$. This is good practice since it prevents excessive loss of slower-growing phage by competition. A 500,000 phage library requires 25 plates of 20,000 mm$^2$ area or about 0.5 m$^2$ of bacterial lawn. In common practice the plaques are grown to nearly confluent lysis and the phage transferred to duplicate 155 mm diameter filters. The phage DNAs are then released by alkali and bound to the filters. The DNA matrix on the filter provides more or less faithful reproduction of the random array of plaques. After appropriate treatment the filters are hybridized with a radioactive probe, washed thoroughly, dried and autoradiographed under X-ray film. A radioactive spot occurring on both duplicates indicates the location of a recombinant phage plaque of interest. A plug containing this plaque and usually also the neighboring plaques is removed, diluted and replated. The filter transfer and hybridization process is repeated and finally the individual phage desired is selected and grown from one of the isolated positive plaques. Each time a library is screened a completely independent random set of plates is prepared.

By the present invention, it has been found that this procedure can be improved by the use of a fixed, reproducible library array in which each plaque has a certain known and recorded position. The advantages of this invention include:

Information storage.

The same library can be screened over and over with different probes, and the location in the fixed array of specific sequences can be stored in the computer as positional information. This information can be made available visually on the output screen, or as hard copy if desired. Thus a genome of interest (e.g., a food plant genome or a given human genome) can be studied extensively over long periods, and knowledge of gene location in the library accumulated. At any time any previously studied gene (and its flanking sequences) is instantly available. Positional library gene location information can easily be shared between all research groups which possess a copy of the initial fixed library array.

Genome mapping.

The ability to store locational information with regard to a genome library leads to special new applications in the area of genome mapping. For example, suppose a moderately repetitive sequence were found in the vicinity of a particular structural gene, as very often occurs in animal genomes (see review in Britten, R. J. and Davidson, E. H. (1979). Science 204. 1052–1059; Davidson, E. H., Hough, B. R., Klein, W. H. and Britten, R. J. (1975). Cell 4, 217–238; Ryffel, G. U., Muellener, D. B., Wyler, T., Wahli, W. and Weber, R. (1981). Nature 291, 429–431; and Scheller, R. H., McAllister, L. B. Crain, W. R., Durica, D. S., Posakony, J. W., Thomas, T. L., Britten, R. J. and Davidson, E. H. (1981). Mol. Cell. Biol. 1, 609–628), and it was desired to determine whether other structural genes expressed coordinately are located near other members of the same repeat family. The repeat sequence would be used as a probe and the locations of all repetitive sequences of that family in the genome stored. Use of a chosen second structural gene probe provides a yes or no answer to whether this gene is located in the vicinity of sequences of the same repeat family. Many problems of this kind are statistical; i.e., the significance of finding repeat sequence in some particular recombinant depends on the repetitive sequence family size. The use of fixed array screening lends itself to accumulation of statistically valid data because virtually all the family members can be observed at once. Since there are probably only a few hundred or at most a few thousand repeat sequence families in a typical animal genome, with a certain amount of work the location of a major fraction of the repeats in the whole genome and their own linkage patterns can be recorded and analyzed. Similarly, linkage of structure tural genes and clustering of genes can be studied very conveniently by fixed array screening. Genome "walking", i.e., identification of overlapping recombinants by successive probe isolation and rescreening, is much facilitated, and with storage of previously found information many unexpected relationships will probably turn up in the course of such exercises. Finally, non-repetitive sequences identified independently as to chromosomal location (Robins, D. M., Ripley, S., Henderson, A. S. and Axel, R. (1981). Cell 23, 29–39; Harper, M. E. and Saunders, G. F. (1981). Chromosoma 83, 431–439) can be labelled in the computer and as a given genome is further studied chromosomal linkage patterns will begin to emerge as well.

Deletion and insertion polymorphism.

There is an increasing evidence that mobile sequence elements are present in animal genomes, and these delete and insert with high frequency. Many investigators suspect that this process is a fundamental driving force in evolution (e.g., see Davidson, E. H. (1981). In: *Evolution and Development*, J. T. Bonner (ed.), Springer-Verlag, Heidelberg (in press). Sequence insertions may also very possibly be involved in carcinogenesis, where they may be the result of viral genome integration. Similarly, a surprisingly large fraction of those mutations that have been studied at a molecular level in Drosophia turn out to be insertion or deletion mutations (e.g., Gehring, W. J. and Paro. R. (1980.) Cell 19, 897–904; Ashburner, M. (1981) In: *Genome Evolution*, G. Dover and R. B. Flavell (eds.), Academic Press, London (in press). Yet little evidence exists as to the actual extent of deletion-insertion polymorphism among the genomes of a given species.

We have now developed an invention which makes it practical to study human genome polymorphism. This is the leading example of the uses to which the system of this invention can be put. By conventional procedures the approach considered would be prohibitively laborious (though not totally impossible). Genome libraries are prepared from several individuals (or e.g., from a given strain of cancer cells). A given individual library consists of a total of 500,000 plaques located at 2 mm spacings in a regular array on eight large (cafeteria tray) agar plates. A fixed array replicator consisting of 62,500 regularly arrayed pins matching the plaque arrays with a precise mechanical locator and lifter are used to pick up phage from an original plate and deposit a few phage from each plaque on other plates for replication of the library (see next section for details). Each of the libaries to be compared is plated in its own fixed array, and then screened repetitively with a series of probes. The probes are chosen to represent sequences that are linked in one of the test genomes in that they completely include the full length of a single DNA segment in a given recombinant plaque. These probes are identified as a, b, c, d, e, f in sequential order. Six replicas of each library are prepared and transferred to nitrocellulose filter sheets twice from each plate to yield duplicates. After lysis, drying, and prehybridization a different set of filters and duplicates is hybridized with each of the six probes. The individual filters are then washed in the usual manner, dried and assayed for radioactive spots using the device of our concurrently filed patent application entitled "Large Area Direct Counting Chamber, Support and Display". The location of these spots is then stored in the computer. After the positions on the 96 filters (in this example) are stored, spots that are not radioactive for both duplicates are deleted from the memory. Then comparisons are made between the different probes. If deletions or substitutions of blocks of sequence distinguish any of the six genomes, plaques which react with external parts of the sequence (e.g., b, c, and e and f) and not with an internal probe (e.g., d) will be found and reported. Finally the computer lists the apparent frequency of repetition of each of the probes, calculated from the number of plaques which react with it, and supplies other useful statistics. It is evident that a series of such measurements with different individual libraries, using different probe regions, indicates the amount of sizeable deletion or substitution events that have occurred in human populations, and give extensive information about the overall patterns of sequence organization. This type of procedure can also be used, of course, to compare the DNA sequences around specific genes in given tissues in order to detect programmed rearrangements, as in the immune system; to study specific mutations; to compare the genomes of different species and subspecies; etc. Comparison of genomes by this method is illustrative of a kind of investigation that heretofore has not been seriously attempted because of the immense labor involved, but which can be carried out to statistical significance by the utilization of the present invention.

The screening and detecting of desired recombinants in cosmid libraries is important (Meyerowitz et al., 1980 Gene 11, 271–282). We have found that by far the most efficient procedure for handling these huge recombinants (about 40 kb per insert) is to carry them on filters as colonies (Hanrahan and Meselson, 1980, Gene 10, 63–67). Much the same procedures as for recombinant phage plaque screening would be useful on cosmid libraries for gene isolation, mapping studies, etc. with the system provided by this invention.

It is known to use velvet cloth blotters for replica plating in bacterial genetics. In work relating to recombinant DNA, it has also been known to use a plurality of nail heads provided by driving about 100 nails into a block of wood, and using the nail heads to replicate a small fraction of a DNA library. The use of velvet blotters or nail heads is quite remote from the present invention. These prior techniques are either very limited in size and number of plaques and/or incapable of precise replication. By their nature, the attempted replicas deviate from the original. In addition, their use is limited to either reproduction of very small arrays with large spacings or would perform unfaithful reproductions of very limited portions of a DNA library. The device of this invention, unlike felt and velvet, picks up small, spacedapart specimens of the individual phage in the lawn.

Felt and velvet do not provide spacing and there is also the problem of convergent growth.

The present invention will be useful in any typical moderate sized molecular biology laboratory or an industrial recombinant DNA laboratory.

SUMMARY OF THE INVENTION

Briefly the present invention comprehends a system for the production and maintenance of genomic libraries and maintenance of genomic libraries of recombinant DNA in a fixed geometric array arranged so that such libraries may be accurately replicated and maintained with the same set of individual DNA inserts occupying reproducible locations and comprising:

(a) sets of individual bacterial colonies or plaques of bacteriophage which contain inserts of animal or plant DNA and are present in so large a number that there will be a high probability that the complete library will contain each DNA sequence of all of the sequences present in an animal or plant genome; to be established in subarrays which can individually be replicated, (b) a subsystem for picking up inocula from each of a geometric array simultaneously and tranferring them to a second similar geometric array, including carrying and aligning means for maintaining a transfer means in superposed relationship with respect and for raising and lowering the transfer means into and out of proximity to said colonies or plaques, and (c) a subsystem for intially establishing such subarrays by transfer from a randomly spread pattern of colonies or plaques of bacteriophage.

It is an object of this invention to prepare a novel device useful in recombinant DNA work.

More particularly, it is an object of this invention to provide a device adapted to replicate recombinant DNA libraries of eukaryotic genomes in fixed arrays.

These and other objects and advantages of this invention will be apparent to those skilled in this art from the more specific descriptive material which follows, having further reference to the accompanying drawings.

DESCRIPTION OF THE PREFERRED EMBODIMENTS OF THE INVENTION

The first step in the preparation of fixed array libraries according to this invention is amplification of the library as a random set of sub-confluent plaques on a set of large agar plates. The initial transfer from this random set of plaques to a fixed array of plaques will be done by means of the fixed array replicator, which will be also used to maintain and further replicate the library.

Turning to the drawing.

Figure 1:
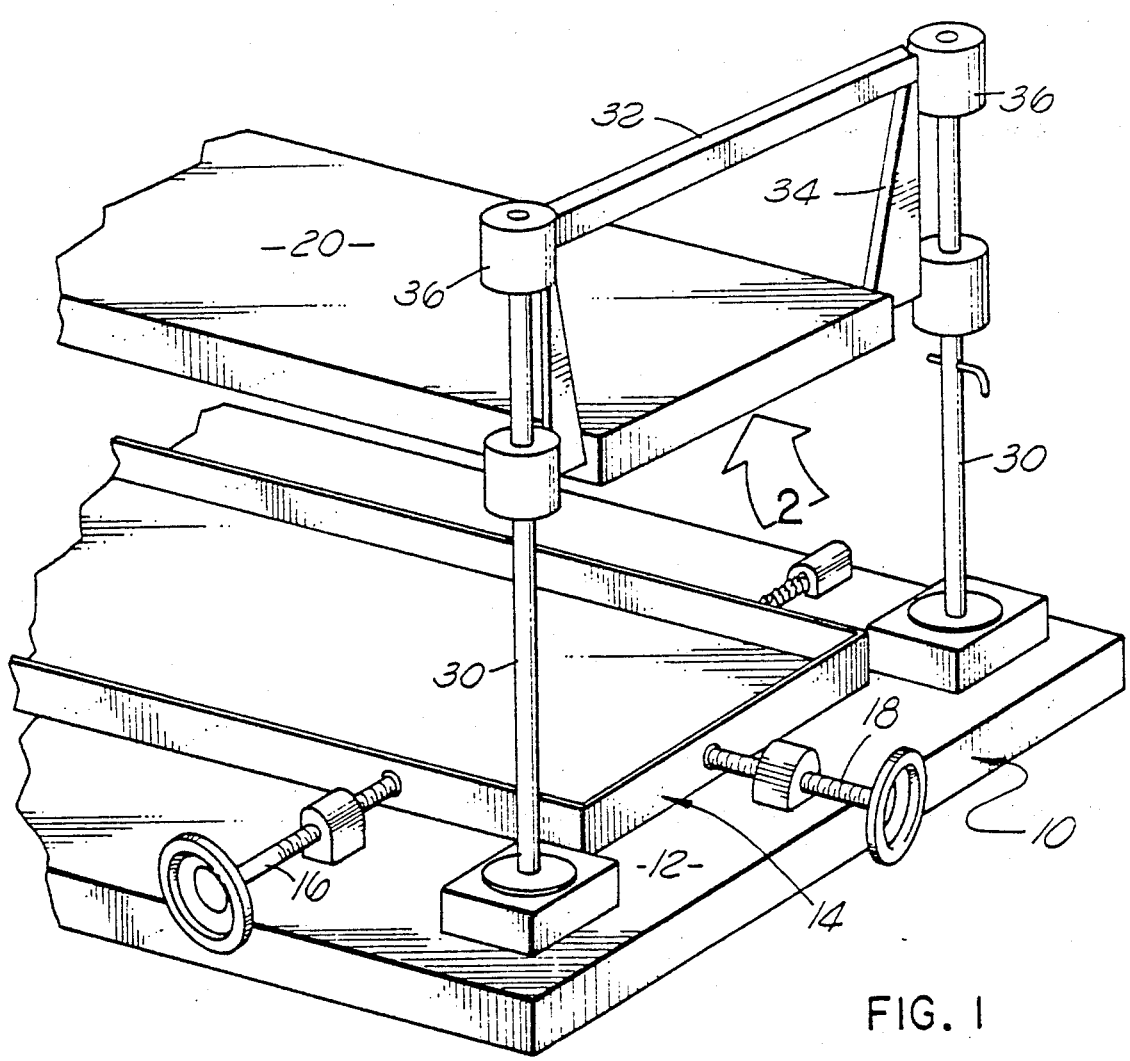
FIG. 1 is a perspective view of the preferred device of this invention.

Considering the drawings in greater detail, in FIG. 1, the base member 10 has a smooth horizontal surface 12 upon which the flat cafeteria tray or plate 14 is adapted to rest. The agar having phage in a fixed array of plaques substantially occupies the tray, the agar not being depicted in the drawings. Micrometerlike adjustments 16 and 18 are provided at each side of tray 14 so that by operation of adjustments 16 and 18, the tray 14 can be slidably moved slightly in either or both the "X" and "Y" directions with respect to base member 10 which member is intended to remain stationary at all times.

Figure 2:
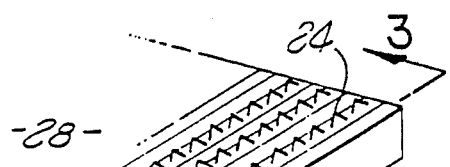
FIG. 2 is a perspective view of the support and pin arrangement used in the device of FIG. 1.
Figure 3:
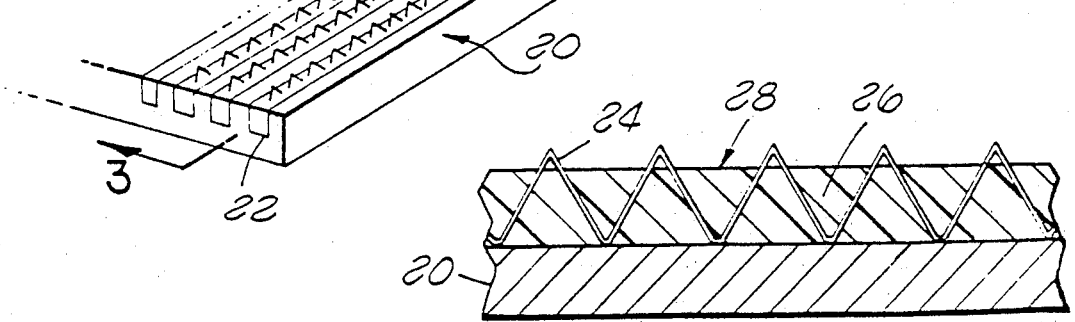
FIG. 3 is a sectional view along the line 3—3 in FIG. 2.
Figure 4:
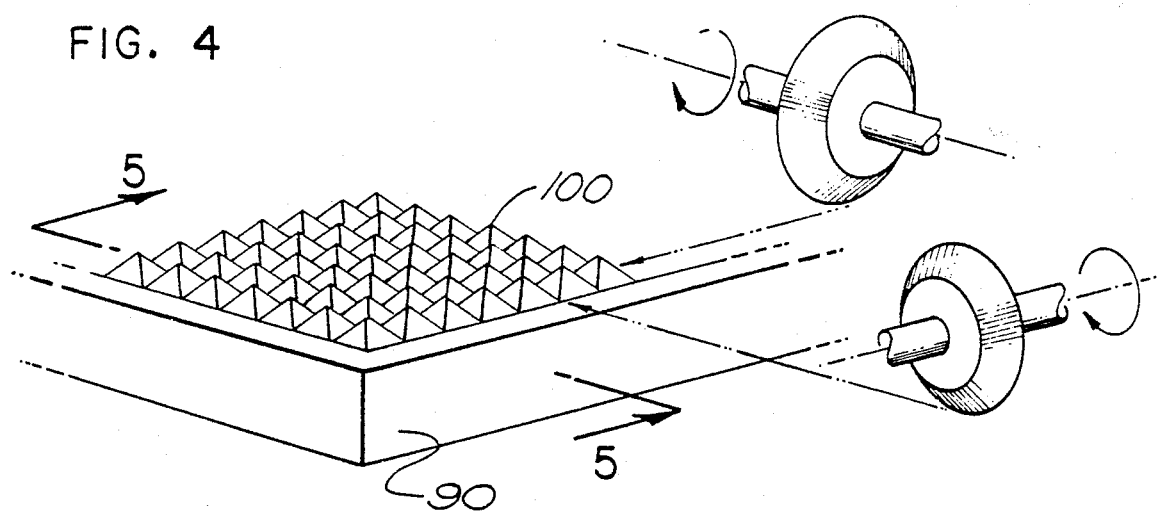
FIG. 4 is a perspective view of another and preferred embodiment of the transfer means.
Figure 5:
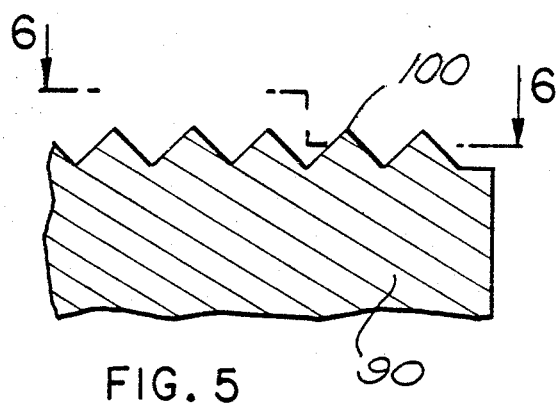
FIG. 5 is taken along the line 5—5 in FIG. 4.
Figure 6:
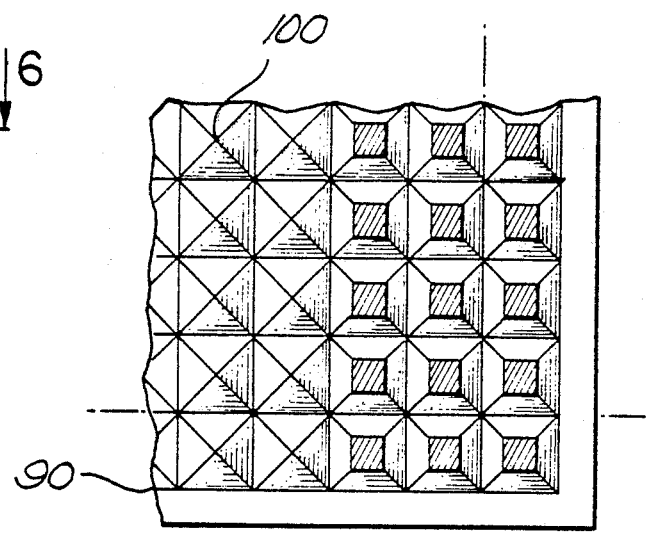
FIG. 6 is taken along the line 6—6 in FIG. 5.
Figure 7:
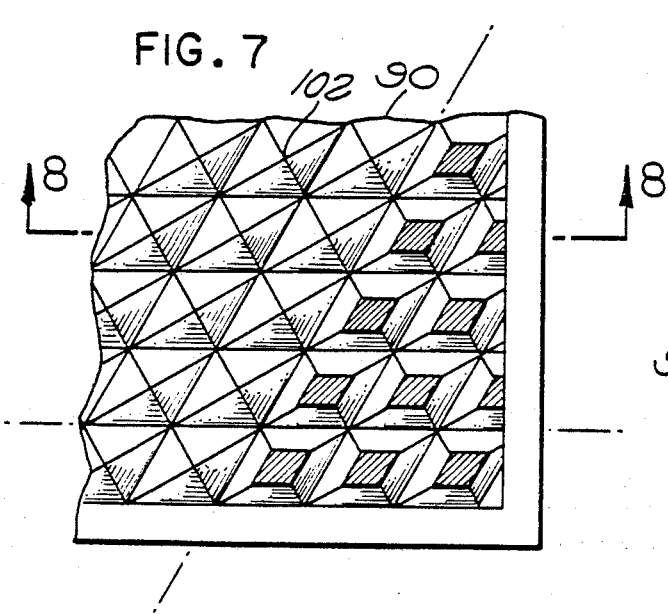
FIG. 7 is a variation of the embodiment of FIGS. 4 to 6.
Figure 8:
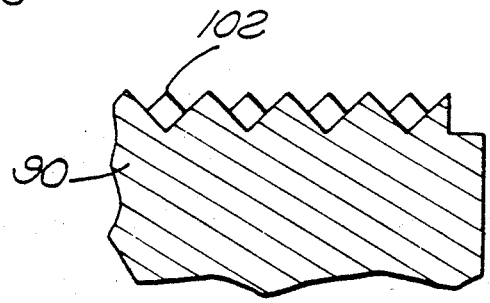
FIG. 8 is taken along the line 8—8 in FIG. 7.

In superposed relationship to the flat plate 14 is a support 20 which is generally coextensive in area and shape with said flat plate 14. As is best shown in FIG. 2, the flat plate has a series on parallel lateral grooves 22 into each of which is received a crimped wire 24. The apexes of the crimped wires 24 project beyond the grooves 22. The grooves are then filled or potted with a hardenable glue or resin 26, as shown in FIG. 3, leaving the free ends of said wires projecting in pin-like fashion from the surface 28 of the support 20.

The fixed array replicator of this invention also includes four vertical corner posts 30 afixed to the base member 10. The posts 30 together with the horizontal structural member 32, vertical members 34 and spools 36, all afixed to support 20, form a carrying and aligning means for maintaining the support 20 in superposed relationship with respect to tray or plate 14 and for lowering and raising the support 20 into and out of proximity to plate 14.

In operation and with agar and plaque present in plate 14, the support 20 is lowered until just the free ends of the wires or pins are slightly immersed in the agar. Then, the support 20 is raised, carrying away phage or bacteria on the pins. A second tray of agar, like that of plate 14, can be substituted and the support 20 lowered to innoculate the new tray.

In the present embodiment, the fixed array replicator consists of more than 50,000 "pins", indentified by reference numeral 24, arrayed at about 2 mm spacings. Such a tool might be square or circular depending on practical requirements for agar plates, filter shapes and the most practical geometry for comouter processing. FIG. 2 shows an example of a square array that is made by crimping wires at 2 mm intervals and assembling them in a block made up of 250 slots. This arrangement covers $\frac{1}{4}$ m$^2$ or 62,500 potential plaques. The most practical size may be larger or smaller than that indicated in FIG. 1. The requirement for the best size and material for the individual transfer pins is simply that enough phage be transferred to assure that each particular plaque is propagated every time a replication is required.

When a library is transferred from a random array to a regular geometric array most spots will contain just one type of phage. In other words, during transfer from a random, nearly confluent pattern only a small fraction of the wires will fall in areas between plaques which are free of phage and a smaller number will fall on boundaries containing more than one type of phage. Subsequent growth may lead to one of the phages predominating by competition. It is possible to measure the optimum degree of confluence for this step. After the regular array is formed it is also possible to manually add phages to those spots in the array which are empty. This process would be a very repetitive task but in a day's time a technician could easily transfer several thousand individual phage from isolated plaques on random plates to empty array spots. Since the fixed array library would be useful over a period of years such manual adjustments might be worth the investment.

For this embodiment we consider a library of 500,000 phage propagated on eight plates (cafeteria tray size) 50 cm by 50 cm. Each plate 14 contains about 62,500 plaques and the fixed array replicator is of matching size as indicated in FIG. 1. In order to conveniently replicate the library on sets of agar plates, the mechanical device maintains the replicator horizontal while it is lowered onto an agar plate and controls the depth of penetration of the pins into the agar. The plate is aligned precisely ($\pm 0.2$ mm) in a holder. A design of one embodiment for this device is shown in FIG. 1. The replicator is then lifted and a fresh plate moved into place. The number of imprintings which can be made from one plate is variable. Using micrometer screw adjustments 16 and 18, a plate can be moved a fraction of a millimeter as each set of phage was picked from it. After the needed set of replicas was made from one plate, the transfer tool is sterilized and the process repeated for each of the eight plates that in this example constitute the library.

This is a proposal to develop a new systematic method to maintain and replicate recombinant DNA libraries of eukaryotic genomes in fixed arrays and to develop new screening methods for such libraries. The libraries will be replicated by means of a device which simultaneously transfers phage from 50,000 or more plaques. Eight or ten such sub-arrays form a library of sufficient size to contain almost all of the sequences in a mammalian genome, and each insert will be located at a fixed "address" in the array. After DNA transfer from the array to a filter and hybridization with a highly labeled probe, the radioactivity is detected by simultaneous large area direct counting of as many as 50,000 precisely defined spots using the spark chamber with high precision location capability, as described in our concurrently filed patent application, now U.S. Pat. No. 4,500,786, issued Feb. 19, 1985. Results are communicated automatically to a computer. Analysis of information communicated to the computer or stored from previous observations on the same fixed array library permits comparison of results obtained with different probes, accumulation of genomic mapping data, measurement of sequence rearrangement frequency, and many other applications. The system is also useful in any molecular biology laboratory for direct analysis of RNA, DNA and protein gel blots, and DNA sequencing gels.

In yet another embodiment, the support comprises, a strong base (for example for the large replicator array: 0.5 m×0.5 m) coated with a thick layer (2 to 5 mm) of partially polymerized plastic having the consistency of a stiff gel. This plastic is able to be polymerized fully to hold the pins rigidly for permanent use. To practice this embodiment, the procedure is to load rows of pins into a magnetic holder arm and insert them row by row into their locations in the array. The simplest way to load the holder arm is to cut the pins from a coil over each of the pin locations in the holder. They are attracted into a well with a funnel top and a closely fitting alignment hole at the bottom. Alternatively the pins can be picked up magnetically from a random heap of premade magnetic pins such as fine wire brads without heads. The picker upper arm has a long U-shaped electromagnet with a narrow gap at the pin row location which can easily draw in and hold pins. The surface of the arm is shielded by plastic with funnel-shaped holes every 2 or 3 mm (at the pin spacing). When premade pins are picked up they are drawn into the funnels while the pin bin is agitated so that pins enter each hole. The alignment hole makes them stand up vertically. A photoelectric device scans the arm and sends it back for more when not all of the holes are filled. The magnetic field is reduced as the arm moves so that second pins attracted to the ends of the first pin or pins lying crosswise are easily shaken off. The arm is moved from the pin bin to the next row needing to be filled with pins. It will lower and insert a row of pins into the gel. Then alternating current is applied to the magnet coil and smoothly reduced to zero as for standard demagnetization. Thus, there is no residual force and the pins are left behind as the arm is smoothly withdrawn. If necessary, the plastic gel can be locally heated with a moving laser beam or focussed infrared heat source to polymerize the plastic for one row before removing the magnetic field. If the heat is well enough focussed the gel will remain penetrable in the next coming row. The pins need only remain accurately vertical and in place until the final polymerization is done after all pin rows are in place. A medium amount of polymerization will give sufficient strength for this purpose.

The flat plate and crimped wire arrangement can be modified in many respects within the scope of our invention. For example, a flat plate can be replaced with a cylindrical roll from which project a large number of radially disposed pins, each of which are adapted to impinge on the agar as described above.

The present invention is adapted to the replication in fixed arrays of bacteria as well as of arrays of bacteriophage.

The agar in the plate is normally about 4 to 5 millimeters thick.

The pins preferably penetrate the exposed or top surface of the agar up to a depth of about one millimeter.

The pins are normally rigid in the sense that they are stiff enough to penetrate the agar without bending and each pin can have a sharpened outer end. The pin at the free end can have a diameter of about one millimeter and more commonly, about one-quarter millimeter.

Turning to the preferred embodiments of FIGS. 4 to 8, the transfer means can be cut or ground out of a block 90 of aluminum or molded from plastic to the configurations shown. The apexes 100 of the pyramids are spaced 1/10 inch apart. The embodiment of FIGS. 7 and 8 differ in that the apexes 102 in one row of pyramids are staggered or shifted from the apexes of the immediately adjoining row. This embodiment provides for easy, low-cost and accurate re-production of the transfer means.

Having fully described the invention, it is intended that it be limited only by the lawful scope of the appended claims.

We claim:

1. A device adapted to replicate recombinant DNA libraries of eukaryotic genomes in fixed arrays comprising:
   (a) container means of a size adapted to contain phage or bacteria in a random array of at least about 50,000 plaques,
   (b) in proximinty to said container means, a multipoint simultaneous transfer means containing at least about 50,000 rigid points having fixed distance between points and being adapted to transfer phage or bacteria from colonies such that locations are precisely maintained, all of the free ends of said points terminating a plane for simultaneous contact with and penetration of the surface containing the phage or colony,
   (c) carrying and aligning means for maintaining said transfer means in superposed relationship with respect to said container means including vertical slide members adjacent corners of said transfer means whereby said transfer means can be slidably moved toward and away from said container means while maintaining the container means and transfer means in essentially constant registry, said container means and transfer means being generally coextensive in area and shape, and said container means being provided with micrometer adjustment and restraining means in both the "X" and "Y" axes for controlled small lateral displacement of said container means with respect to said transfer means and said carrying and aligning means, and
   (d) a base member, wherein said vertical slide members, said container means and said adjustment and restraining means are carried by said base member.

2. The device of claim 1 wherein the multipoint simultaneous transfer means is a flat support to which a large number of pins are affixed.

3. The device of claim 2 wherein the pins are spaced uniformly from each other at a spacing of about 2 millimeters.

4. The device of claim 2 wherein the pins are in the form of crimped wires and said free ends are the apexes of said crimped wires, and wherein the pins are affixed to the support with epoxy resin.

5. The device of claim 1 wherein the multipoint simultaneous transfer means is a flat support having a plurality of identical pyramids projecting upwardly therefrom said pyramids being uniformly spaced.

6. The device of claim 5 wherein the pyramids are spaced at about 1/10 of an inch at their apexes, said pyramids and the support are integrally formed, and the apexes of one row or pyramids are staggered with respect to the apexes of the pyramids of immediately adjoining rows.

* * * * *